BEGONIA PLANT
Filed June 12, 1972 3 Sheets-Sheet 1
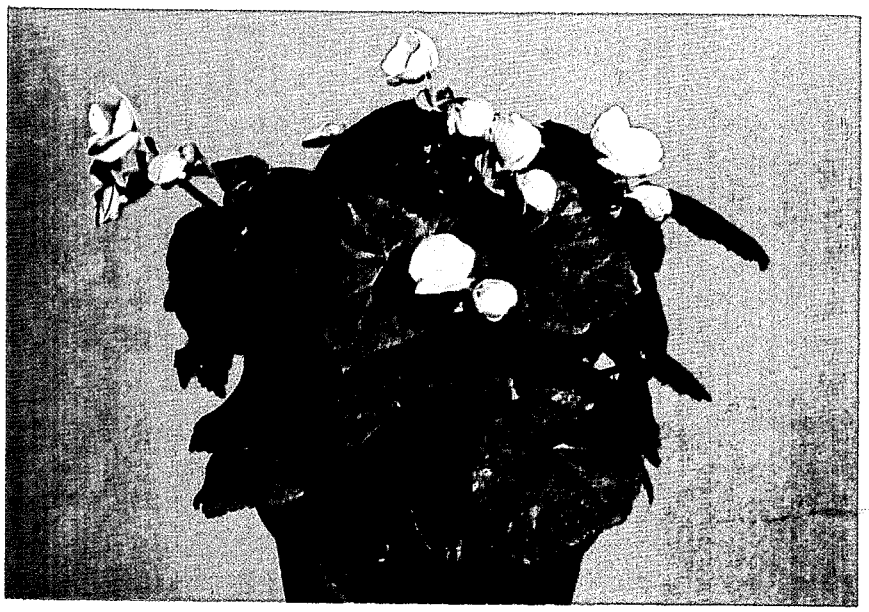

BEGONIA PLANT
Filed June 12, 1972
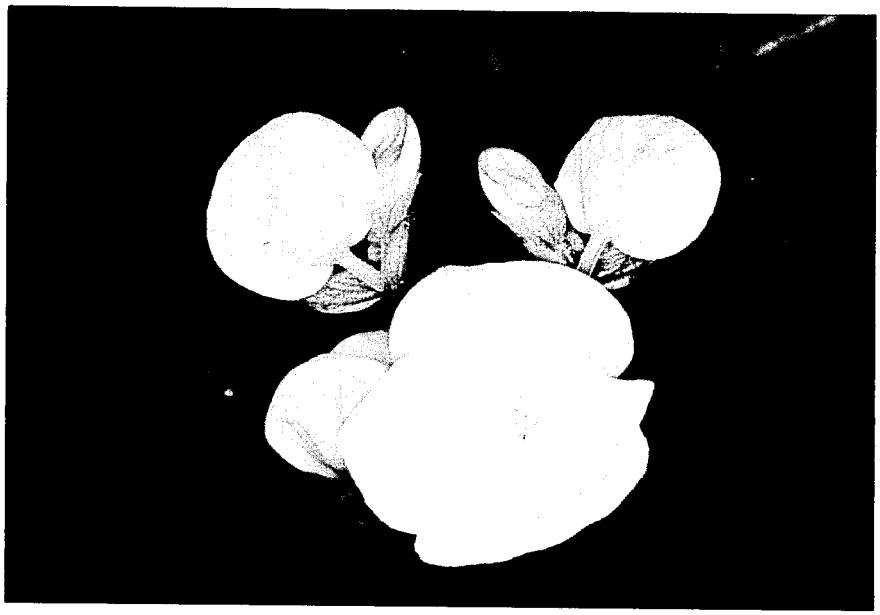

BEGONIA PLANT
Filed June 12, 1972 3 Sheets-Sheet 3
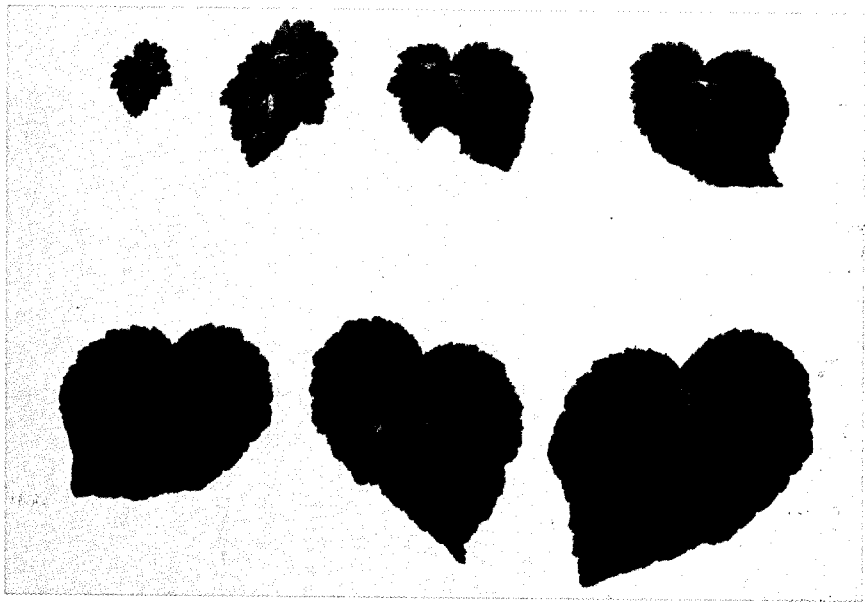

United States Patent Office

Plant Pat. 3,474
Patented Feb. 12, 1974

3,474
BEGONIA PLANT

Bruno Bernstein, Bad Segeberg, Germany, assignor to Mikkelsens, Inc., Ashtabula, Ohio Filed June 12, 1972, Ser. No. 262,087
Int. Cl. A01h 5/00
U.S. Cl. Plt.—68 1 Claim The present invention relates to a new and distinctive variety of begonia plant botanically known as *Begonia elatior* discovered by me as a color mutation of a non-commercial mutation from the Rieger begonia variety Lochsorange, the parentage of which is not known to the inventor. This mutation was found in my nurseries in 2360 Bad Segeberg, Ziegelstrasse 25–27, West Germany. Through asexual reproduction originally of terminal and stem cuttings and then ultimately with leaf cuttings, it has been determined after extensive propagations that this mutation maintains its distinctive characteristics.

The most distinguishing characteristics of this new begonia are the soft yellow color of its flowers; the ease of propagating leaf cuttings; and the very high number (olten 10 or more) of basal adventitious shoots that develop within a relatively short time after leaf cuttings have been struck. The production of high numbers of adventitious shoots from the base of the leaf petiole in the propagation bed is of significant economic importance to the propagator and the ultimate grower finishing the plant for the consumer markets.

The following characteristics distinguish the new variety from other commercial begonia cultivars of this general type:

(1) Medium size single type light yellow flowers having generally four petals uniformly initiating throughout the plant.

(2) Plant height considerably shorter than the commercially well-known Rieger varieties.

(3) A very full plant form with an unusually high number of basal shoots.

(4) The foliage is small, oval, and lacking in sharp indentations. Leaves tend to be oval shaped.

(5) Individual stems are thin but firm enough to be self supporting.

(6) Rooting is very rapid.

(7) Initiation of basal adventitious shoots is extremely high. Frequently young plants can be divided to increase plant production and at the name time excessive shoots can be thinned out for quality development.

(8) Flowering can be controlled by properly altering the environmental conditions such as the length of photo periods, especially if plants are developed under long days from leaf propagations.

(9) Properly cultured flowering plants may be used for outdoor beautification because the new variety is more resistant to botrytus and mildew when compared to other begonias of this type.

The new cultivar is illustrated in the accompanying colored photographic drawings in which Sheet 1 is a photograph of the overall plant; Sheet 2 is a closeup of the blooms and buds, and Sheet 3 illustrates typical foliage from immature to mature stages. The colors in the photographs are as true as reasonably possible in colored photographs of this type.

The following detailed description of the new variety is founded on considerable observations and evaluations made of the new variety grown by me using established horiticultural techniques in my nursery in Bad Segeberg, West Germany. Color references are to the Royal Horticultural Society Colour Chart, except where general color terms of ordinary significance may be used. References in the description to the cultivar Schwabenland refer to the cultivar disclosed and claimed in the pending application for U.S. plant patent Ser. No. 158,640, filed June 30, 1971, by Gertrude Rieger, legal representative, for the deceased inventor Otto Rieger.

Parentage: A mutation from a previous non-commercial mutation of the begonia cultivar Riegers Lochsorange. The mutation occurred on a shoot in a flowering plant of this mutation in my nursery at Bad Segeberg, West Germany.

Propagation: Leaf cuttings have been propagated consecutively and sequentially for several generations demonstrating that the unique characteristics of this variety remain true to type. Leaf cuttings propagated at 21°–22° C. will begin to root in approximately 14 day and adventitious buds will be visible in 21–28 days. The development of the adventitious shoots through the propagation media to the surface will be well advanced in six weeks time. The new variety propagates considerably faster than the cultivar Schwabenland and other Rieger varieties, but takes several weeks longer to develop into a marketable plant.

Rooting habit: Roots initiate quickly and develop abundantly into a fine interlacing texture in loose, well aerated, highly organic composts.

Plant form: Plants are short, compared to Schwabenland, but very compact and full as a result of the abundant development of basal adventitious shoots from the leaf petiole.

Habit of growth: Plants generally develop in an upright position without any additional support. The rate of growth is considerably slower than in Schwabenland.

Blooming habits season: Normal natural flowering is in late November or early December, if plants are grown at 18° C. in late September or early October. When vegetative propagation using leaf cuttings is practiced, precision flowering programs can be established for year around commercial production by manipulating environmental factors, especially temperature and day-length. Flowering response is continuous for several months. The soft yellow color of the blooms can be maintained if the flowering plants are grown in a shaded area. Plants can be grown outside in the summer under protected shaded areas in temperate climates.

Foliage: Leaves are borne alternately on the stems at a close angle. Plant stems and leaf petioles are light yellowish green. The leaves tend to be a dull green without any striking characteristics such as shape or iridescence as displayed by the cultivar Schwabenland.

*Size.*—Foliage is small to medium, measuring approximately four to six centimeters in diameter at maturity, when compared to other established begonia cultivars. General plant conditions and environmental factors can greatly alter the size, shape, and color of the foliage.

*Shape.*—Oval but somewhat oblong having the greater diameter in the area of the leaf petiole. There are no sharp indentations.

*Texture.*—Upper side is smooth, dull, having a general leathery feeling but not waxy or with a high sheen. Underside is glossy and waxy to the feel.

*Margin.*—There are no sharp indentations of any depth. Marginal serration is evident but is a minor identification. Lobing in the leaf petiole area may occur on either side.

*Color.*—There is red pigmentation infused into the leaf that causes considerable difficulty in close identification of the exact shade of green. New foliage upper side is green near RHS 146 A/B, underside is a light green/red; Mature foliage: upper side is green near RHS A/B, underside is near 148–B.

Flowers: Blooms are single with four light yellow petals.

*Borne.*—On continuously flowering trusses. Individual blooms last several weeks from the bud stage to senescence, with overall flowering continuing over several months.

*Quantity.*—This variety is not as floriferous under adverse growing conditions of the winter months as other Rieger types. Quantity of blooms is sufficient at all times to make an attractive flowering plant.

*Petals Color.*—Upon first opening, the upper side of the petals approach yellow RHS 9A, fading at maturity to near yellow RHS 6A. Near the period of senescence the color will approach yellow 2–C. Frequently the petals will have some streaking of deeper tones of yellow. The underside of the petal is a lighter tone at all stages of development compared to the upper side. Light intensity and temperature can greatly alter the development and coloration of the blooms at any particular time of the year.

*Buds.*—In early stages are an ivory white approximately one to one and a half centimeters in diameter, are flat and round as a small coin.

*Reproductive organs.*—Stamens are quite plentiful developing an attractive dark yellow eye in the center of the blooms. *Stamens*: color approaches RHS 14–A/B. *Pollen*: RHS 7A.

No styles or ovaries have been seen to date.

Disease resistance: The new variety is somewhat more susceptible to Xanthomonas than other commercially utilized cultivars. The flowers and foliage are quite resistant to common powdery mildew and botrytus when compared to the melior type begonias.

I claim:

1. A unique and distinct cultivar of *Begonia elatior* characterized particularly by its short, compact, and full growth; its soft light yellow flowers; its extreme ease of propagation from small leaf cuttings that develop a very high number of adventitious shoots, which phenomenon is of significant economic importance to the grower; its good resistance to powdery mildew and botrytus allowing the variety to be used in outdoor plantings; its capability of being produced for flowering crops on a year around basis by leaf propagation and controlled environmental conditions; and by its long lasting and long flowering qualities in the home when properly handled.

No references cited.

ROBERT E. BAGWILL, Primary Examiner

UNITED STATES PATENT OFFICE
CERTIFICATE OF CORRECTION

Patent No. PP-3474 Dated February 12, 1974

Inventor(s) BRUNO BERNSTEIN

It is certified that error appears in the above-identified patent and that said Letters Patent are hereby corrected as shown below:

Column 1, line 22, change "alten" to --often--; line 46, change "name" to --same--.

Column 2, line 31, between "habits" and "season" insert a slash --/--; line 69, between "RHS" and "A/B" insert --147--.

Signed and sealed this 4th day of June 1974.

(SEAL)
Attest:

EDWARD M.FLETCHER,JR.
Attesting Officer

C. MARSHALL DANN
Commissioner of Patents

USCOMM-DC 60376-P69
* U.S. GOVERNMENT PRINTING OFFICE : 1969 O—366-334